United States Patent
Feurer et al.

(10) Patent No.: US 6,444,613 B1
(45) Date of Patent: Sep. 3, 2002

(54) DEFOLIANT

(75) Inventors: Gerhard Feurer, Liederbach; Christopher Rosinger, Hofheim; Alfred Angermann, Kriftel/Ts.; Felix Thürwächter, Bad Homburg; Werner Schlesinger, Flörsheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/522,213

(22) Filed: Mar. 9, 2000

(30) Foreign Application Priority Data

Mar. 12, 1999 (DE) .......................... 199 11 165
Oct. 26, 1999 (DE) .......................... 199 51 428

(51) Int. Cl.[7] .................... A01N 43/40; A01N 43/56; A01N 43/66; A01N 47/30; A01N 47/36
(52) U.S. Cl. ................ 504/129; 504/130; 504/134; 504/136; 504/139
(58) Field of Search ................ 504/129, 130, 504/132, 134, 136, 137, 139

(56) References Cited

U.S. PATENT DOCUMENTS

| | | |
|---|---|---|
| 4,613,354 A | 9/1986 | Rusch et al. .......... 71/73 |
| 5,045,105 A | 9/1991 | Grossmann et al. ......... 71/74 |
| H1764 H | * 12/1998 | Hotzman et al. .......... 504/116 |

FOREIGN PATENT DOCUMENTS

| | | |
|---|---|---|
| AU | 624730 | 2/1991 |
| DE | 198 34 629 | 12/1998 |
| EP | 0 787 429 | 8/1997 |
| GB | 1 594 148 | 10/1997 |

OTHER PUBLICATIONS

Database Accession No. 131:55108, Lemon, Robert G. et al, "Evaluation of CGA–248757 (Action) as a Harvest–Aid in Central Texas", Proc.—Beltwide Cotton Conference, 1999, vol. 1, pp. 605–606; also referred to as XP002153390.
Smith et al, Beltwide Cotton Conference 1996, Abstracts, p. 1159.

* cited by examiner

*Primary Examiner*—S. Mark Clardy
(74) *Attorney, Agent, or Firm*—Frommer Lawrence & Haug

(57) ABSTRACT

A mixture, comprising
 (A) thidiazuron or thidiazuron and diuron and
 (B) one or more PPO inhibitors of the formula (I)

$$W-V \qquad (I),$$

where the symbols have the meanings given in the description, is suitable for effecting leaf abscission of plants, in particular cotton plants.

16 Claims, No Drawings

DEFOLIANT

The invention relates to the field of defoliants, in particular thidiazuron-comprising mixtures, and their use in crops of cotton.

Thidiazuron has been known for some time as a defoliant, in particular for use in crops of cotton (see, for example, "The Pesticide Manual", 11th edition, British Crop Protection Council, Farnham 1997).

The use of thidiazuron in mixtures has also been described, see, for example, DE-A2646712.

However, since the economical and ecological demands placed on modem defoliants are constantly being raised, for example with respect to effect, application rate, residues, toxicity and favorable manufacturing, there exists the permanent task of developing, for example by combining known active ingredients, novel defoliants which offer, at least in some areas, advantages compared with the known compounds.

Surprisingly, it has now been found that thidiazuron in mixtures with certain herbicides which inhibit the activity of the enzyme protoporphyrinogen-(IX) oxidase (PPO inhibitors) has synergistic effects.

EP-A 0 412 364 and DE-A 39 05 916 describe or propose diphenyl ether or N-phenyl-3,4,5,6-tetrahydrophthalimide derivatives in mixtures with thidiazuron.

However, a connection between the defoliant effect and the herbicidal mechanism of action of the compounds is not established.

EP-A 0 787 429 describes 3-substituted phenylpyrazoles as defoliants, possible mixtures with thidiazuron are not mentioned.

Smith et al. (1996 Beltwide Cotton Conference, Abstracts, p. 1159) report about fluthiacet-methyl as defoliant, without discussing mixtures with other active ingredients.

DE-A 198 34 629 describes a mixture of thidiazuron and fluthiacet-methyl for use as a herbicide.

The present invention accordingly provides the use of a mixture comprising (A) thidiazuron or thidiazuron and diuron and
(B) one or more PPO inhibitors of the formula (I)

$$W—V \qquad (I),$$

for effecting leaf abscission of plants,
where the symbols in the formula (I) have the following meanings:

W is a cyclic group W-1 to W-23

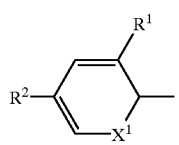

W-1

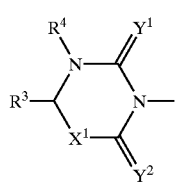

W-2

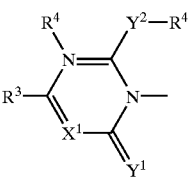

W-4

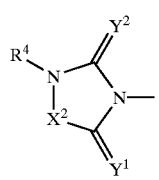

W-5

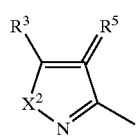

W-6

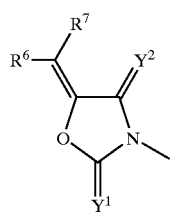

W-7

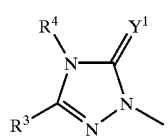

W-8

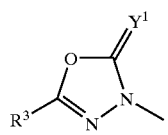

W-9

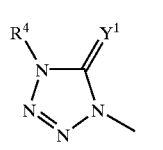

W-10

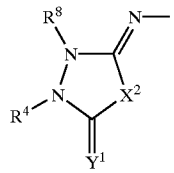

W-11

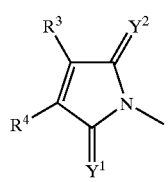

W-12

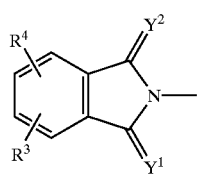
W-13
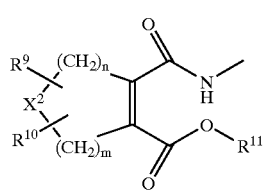
W-14
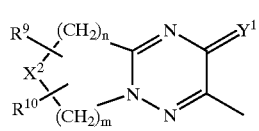
W-15
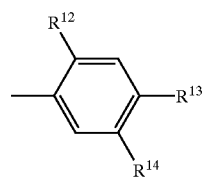
W-16
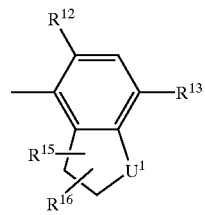
W-17
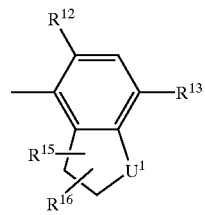
W-18
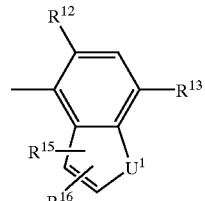
W-19
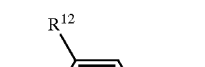
W-20
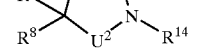
W-21
W-22
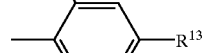
W-23
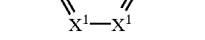
V is one of the groups V-1 to V-11
V-1
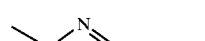
V-2
V-3
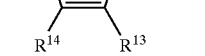
V-4
V-5
V-6

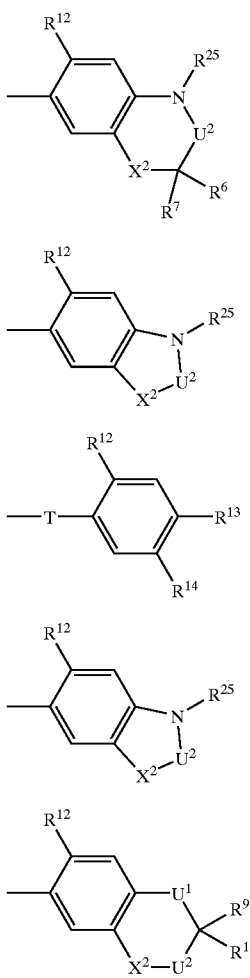

R¹ is hydrogen or halogen;
R² is halogen, alkyl, alkoxy, haloalkoxy or haloalkyl;
R³ is hydrogen, alkyl, haloalkyl, alkoxy, haloalkoxy, alkyl-S(O)$_n$—, dialkylamino, alkylamino, amino or halogen;
R⁴ is hydrogen, alkyl, haloalkyl, alkenyl, haloalkenyl, alkynyl, haloalkynyl, formyl, alkyl-CO— or amino;
R⁵ is hydrogen, halogen, alkyl, haloalkyl or nitro;
R⁶ is hydrogen, alkyl or haloalkyl;
R⁷ is hydrogen, alkyl or haloalkyl;
R⁸ is hydrogen, alkyl, haloalkyl, alkenyl, haloalkenyl, alkynyl or haloalkynyl;
R⁹ is hydrogen, alkyl, halogen, alkoxy, haloalkyl, haloalkoxy, alkoxycarbonyl, haloalkoxycarbonyl or amino;
R¹⁰ is hydrogen, alkyl, halogen, alkoxy, haloalkyl, haloalkoxy, alkoxycarbonyl, haloalkoxycarbonyl or amino;
R¹¹ is hydrogen or alkyl;
R¹² is hydrogen, alkyl or halogen;
R¹³ is hydrogen, halogen, alkyl, haloalkyl, alkoxy, haloalkoxy, cyano, nitro, amino, alkylamino, dialkylamino, alkoxycarbonyl, —(C=O)NH₂, —(C=S)NH₂, hydroxyl, acyloxy, substituted phenyl, substituted phenoxy, substituted benzyl or substituted benzyloxy;
R¹⁴ is hydrogen, alkyl, haloalkyl, alkoxyalkyl, haloalkoxyalkyl, alkenyl, haloalkoxyalkenyl, alkynyl, haloalkynyl, alkoxy, haloalkoxy, haloalkenyloxy, alkynyloxy, haloalkynyloxy, halogen, —O—COR¹⁵, —OH, —S(O)$_n$R¹⁵, —COR¹⁷, —CONR¹⁸R¹⁹, —CO₂R²⁰, —(CR⁶R⁷)$_n$—CO₂R²⁰, —CR²¹=CR²²CO₂R²⁰, —CN, —CR¹¹(X¹R²³)(X²R²⁴), —NR¹¹—(CR⁶R⁷)$_n$—CO₂R²⁰, —O—(CR⁶R⁷)$_n$—CO²R²⁰, —S(O)$_n$—CR²¹=CR²²—C(O)NR¹⁶R¹⁷, —(NR⁶R⁷)$_n$CONR¹⁶R¹⁷—(CR⁶R⁷)$_n$—CO₂R²⁰, —NO₂, —NR¹⁶R¹⁷, —NR²⁴SO₂R¹⁵ or —NR²³COR¹⁵;
R¹⁵ is hydrogen, M, alkyl, haloalkyl, alkenyl, haloalkenyl, alkynyl, haloalkynyl or halogen;
R¹⁶ is hydrogen, alkyl, haloalkyl, alkenyl, haloalkenyl, alkynyl, haloalkynyl or halogen;
R¹⁷ is hydrogen, OH, OM, alkyl, haloalkyl, alkenyl, haloalkenyl, alkynyl, haloalkynyl, alkoxyalkyl or haloalkoxyalkyl;
R¹⁸ is hydrogen, alkyl, alkoxy, alkenyl, haloalkenyl, alkynyl or haloalkynyl;
R¹⁹ is hydrogen, alkyl, alkoxy or
R¹⁸ and R¹⁹ together with the nitrogen atom form a 5-, 6- or 7-membered ring which may be interrupted by oxygen or sulfur;
R²⁰ is hydrogen, M, alkyl, haloalkyl, alkenyl, haloalkenyl, alkynyl, haloalkynyl, alkoxyalkyl, haloalkoxyalkyl or —(CR⁶R⁷)$_n$—CO₂R¹⁵;
R²¹ is hydrogen, alkyl, halogen or CN;
R²² is hydrogen, alkyl, halogen or CN;
R²³ is hydrogen or alkyl;
R²⁴ is hydrogen, alkyl or
R²³ and R²⁴ together are a substituted or else unsubstituted 5-, 6- or 7-membered cyclic acetal or thioacetal;
R²⁵ is hydrogen, alkyl, alkoxy, alkenyl, haloalkenyl, alkynyl, haloalkynyl, carbamoyl or thiocarbamoyl;
M is an alkali metal, alkaline earth metal or ammonium ion;
X¹ is identical or different and is C-R⁵ or N;
X² is identical or different and is CR²R⁶, O, —S(O)$_n$— or NR²⁵;
Y¹ is O or S;
Y² is O or S;
n, m are 0, 1 or 2;
U¹ is O, S(O)$_n$, NR²³ or CR⁹R¹⁰;
U² is S(O)$_n$, CR⁹R¹⁰ or C=O;
T is CR²R⁶, NH or NR².

The invention also provides defoliants or compositions for effecting leaf abscission of plants, comprising one of the mixtures described above, and a process for effecting the leaf abscission of plants, where the plants are treated with one of the abovementioned mixtures or a composition according to the invention.

The invention furthermore provides the abovementioned mixtures themselves, except for mixtures of thidiazuron or thidiazuron and diuron and fluthiacet-methyl.

The abovementioned mixtures are suitable in particular for use in crops of cotton, for example by rapid and/or increased activity or reduced application rates.

For the purpose of the invention, the term defoliant is synonymous with "desiccant" and also embraces the known growth-regulating effect of thidiazuron and of mixtures comprising thidiazuron.

The abovementioned mixtures preferably comprise synergistically effective amounts of the component (A) and synergistically effective amounts of the component (B).

In the above formula (I), "halogen" is to be understood as a fluorine, chlorine, bromine or iodine atom;

the term "alkyl" is preferably an unbranched or branched hydrocarbon radical having 1 to 6 carbon atoms, for example the methyl, ethyl, propyl, isopropyl, 1-butyl, 2-butyl, 2-methylpropyl, tert-butyl, pentyl, 2-methylbutyl, 1,1-dimethylpropyl or hexyl radical;

the term "alkyl" is also preferably a $(C_{3-8})$-cycloalkyl group, for example the cyclopropyl, cyclobutyl, cyclopentyl, cyclohexyl, cycloheptyl or cyclooctyl group;

the term "haloalkyl" is preferably an alkyl group mentioned under the term "$(C_1-C_6)$-alkyl", in which one or more hydrogen atoms are replaced by the abovementioned halogen atoms, preferably by chlorine or fluorine, for example the trifluoromethyl group, the 1-fluoroethyl group, the 2,2,2-trifluoroethyl group, the chloromethyl, fluoromethyl group, the difluoromethyl group or the 1,1,2,2-tetrafluoroethyl group;

the term "haloalkyl" is also preferably $(C_{3-8})$-halocycloalkyl, i.e. one of the $(C_{3-8})$-cycloalkyl radicals listed above in which one or more, in the case of fluorine optionally also all, hydrogen atoms are replaced by halogen, preferably by fluorine or chlorine, for example the 2,2-difluoro- or 2,2-dichlorocyclopropane group or the fluorocyclopentane radical;

the term "alkenyl" is preferably $(C_2-C_6)$-alkenyl, for example the vinyl, allyl, 2-methyl-2-propenyl or 2-butenyl group;

the term "haloalkenyl" is preferably a $(C_2-C_6)$-alkenyl group in which the hydrogen atoms are partially or in the case of fluorine also fully replaced by halogen, preferably by fluorine or chlorine;

the term "alkynyl" is preferably $C_2-C_6$-alkynyl, for example the ethynyl, propargyl, 2-methyl-2-propynyl, 2-butynyl-, 1-pentynyl, 2-pentynyl-, 3-pentynyl- or 4-pentynyl group;

the term "haloalkynyl" is preferably a $(C_2-C_6)$-alkynyl group in which the hydrogen atoms are partially, in the case of fluorine also fully, replaced by halogen atoms, preferably by fluorine or chlorine;

the term "alkoxycarbonyl" is preferably $(C_1-C_6)$-alkoxycarbonyl, for example the methoxycarbonyl, ethoxycarbonyl, propoxycarbonyl, butoxycarbonyl, pentyloxycarbonyl or the hexyloxycarbonyl group;

the term "haloalkoxycarbonyl" is a $(C_1-C_6)$-alkoxycarbonyl group in which one or more, in the case of fluorine optionally also all, hydrogen atoms are replaced by halogen, preferably by fluorine or chlorine;

the term "alkoxy" is preferably an alkoxy group having 1–6 carbon atoms whose hydrocarbon radical has the meaning given under the term "$(C_1-C_6)$-alkyl";

the term "alkylamino" is preferably $(C_1-C_6)$-alkylamino, for example the methylamino, ethylamino, propylamino, isopropylamino, butylamino, isobutylamino, sec-butylamino, pentylamino or the hexylamino group;

the term "dialkylamino" is preferably $(C_1-C_6)$-dialkylamino, for example the dimethylamino, methylethylamino, diethylamino, dipropylamino, dibutylamino, dipentyl- or the dihexylamino group, but also cyclic systems, such as the pyrrolidino or piperidino group;

the term "haloalkoxy" is preferably a $(C_{1-6})$-haloalkoxy group whose halohydrocarbon radical has the meaning given under the term "$(C_1-C_6)$-haloalkyl";

the term "alkoxyalkyl" is preferably $(C_1-C_6)$-alkoxy-$(C_1-C_6)$-alkyl, for example a 1-methoxyethyl group, a 2-methoxyethyl group, a 2-ethoxyethyl group, a methoxymethyl or ethoxymethyl group, a 3-methoxypropyl group or a 4-butoxybutyl group;

the term "haloalkoxyalkyl" is preferably $(C_{1-6})$-haloalkoxy-$(C_1-C_6)$-alkyl, $(C_1-C_6)$-alkoxy-$(C_1-C_6)$-haloalkyl and $(C_1-C_6)$-haloalkoxy-$(C_1-C_6)$-haloalkyl, $(C_1-C_6)$-alkoxy-$(C_1-C_6)$-alkyl radicals having the abovementioned meanings, where one or more, in the case of fluorine optionally also all, hydrogen atoms of the corresponding hydrocarbon radicals are replaced by halogen, preferably by chlorine or fluorine;

and the term "acyl" is the radical of an organic acid, for example the radical of a carboxylic acid and radicals of acids derived therefrom, such as thiocarboxylic acid, unsubstituted or N-substituted iminocarboxylic acids or the radical of carbonic monoesters, unsubstituted or N-substituted carbamic acid, sulfonic acids, sulfinic acid, phosphonic acids, phosphinic acids. Acyl is, for example, formyl, alkylcarbonyl such as $[(C_1-C_4)$ alkyl]-carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals can in each case be substituted further in the alkyl or phenyl moieties, for example in the alkyl moiety by one or more radicals selected from the group consisting of halogen, alkoxy, phenyl and phenoxy.

The illustration given above applies correspondingly to homologs and radicals derived therefrom.

The present invention embraces the use of compounds of the formula (I) in the form of the free base or an acid addition salt. Acids which can be used for forming salts are inorganic acids, such as hydrochloric acid, hydrobromic acid, nitric acid, sulfuric acid, phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula (I) have one or more asymmetrical carbon atoms or stereoisomers on double bonds. Accordingly, enantiomers or diastereomers may be present. The invention embraces both the pure isomers and mixtures thereof. The mixtures of diastereomers can be separated into the components by customary methods, for example by selective crystallization from suitable solvents or by chromatography. Racemates can be resolved into the enantiomers by customary methods, for example by salt formation with a chiral, enantiomerically pure acid, separation of the diastereomeric salts and liberation of the pure enantiomers using a base.

The preferred component (A) is thidiazuron.

In Table 1 below, combinations W—V and the substance classses derived therefrom are listed as preferred examples for the component (B):

TABLE 1

| Formula | Structure type | Combination pattern W-V | Name of the substance class |
|---|---|---|---|
| (Ia) | | W-1/V-1 | 2-phenylpyridines |
| (Ib) | | W-2/V-1 | N-phenyluracils |
| (Ic) | | W-9/V-1 | 3-phenyl-1,3,4-oxadiazol-2(3H)-ones |
| (Id) | | W-6/V-1 | 3-phenylpyrazoles |
| (Ie) | | W-7/V-1 | 3-phenyl-2,4-oxazolidinediones |
| (If) | | W-1/V-6 | 1-(2-pyridyl)-pyrazoles |
| (Ig) | | W-1/V-6 | 1-phenylpyrazoles |
| (Ih) | | W-6/V-6 | 1-(3-pyrazolyl)-pyrazoles |

TABLE 1-continued

| Formula | Structure type | Combination pattern W-V | Name of the substance class |
|---|---|---|---|
| (Ii) | | W-17/V-1 | 5-phenylimino-1,3,4-thidiazolin-2-ones |
| (Ij) | | W-8/V-1 | 2-phenyl-1,2,4-triazolin-3-ones |

The symbols and indices are as defined in the formula (I). Particularly preferred mixing partners (B) are the compounds listed below in Table 2:

TABLE 2

| Structural formula | Chemical Name or Code No. | Technical description |
|---|---|---|
| | F-5231 | WO 85/01939 |
| | nipyraclofen | EP-A-0 154 115 |
| | KPP-300 | WO 87/02357 |

TABLE 2-continued

| Structural formula | Chemical Name or Code No. | Technical description |
|---|---|---|
| | pyrazogyl (proposed) or pyraclonil (proposed) | WO 94/08999 |
| | sulfentrazones | GB-A 2 230 261 |
| | pentoxazones | WO 87/02357 |
| | flupropacil | CH 87-2330 WO 88/10254 |
| | M&B-39279 | GB-A 81-22146 |
| | thidiazimin | EP-A 0 311 135 |
| | carfentrazone-ethyl | WO 90/02120 |

TABLE 2-continued
| Structural formula | Chemical Name or Code No. | Technical description |
|---|---|---|
| 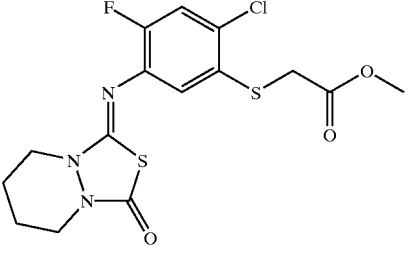 | fluthiacet-methyl | U.S. Pat. No. 4,885,023<br>EP-A 0 273 417 |
| 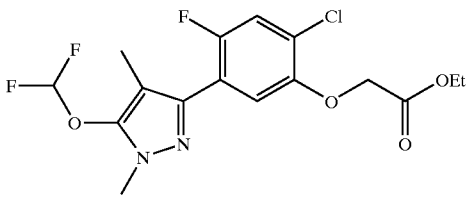 | pyraflufen-ethyl | EP-A 0 361 114<br>JP-A 88-217164 |
| 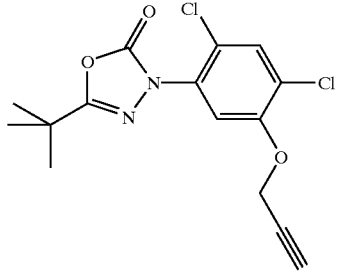 | oxadiargyl | DE-A 2 227 012 |
| 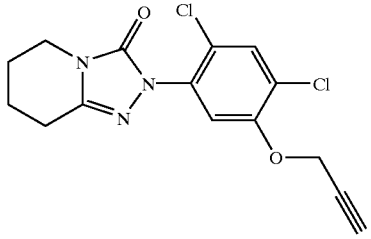 | azafenidine | DE-A 2 801 429<br>U.S. Pat. No. 5,332,718 |
| 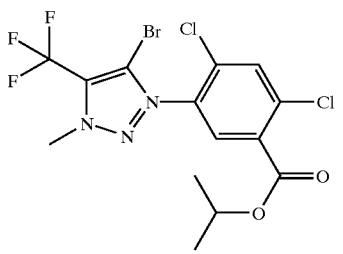 | fluazolate | WO 92/06962 |

TABLE 2-continued

| Structural formula | Chemical Name or Code No. | Technical description |
|---|---|---|
| | butafenacil or fluobutracil (proposed) | WO 91/00278 |
| | oxadiazon | GB-A 1,110,500 |
| | benzfendizone (proposed) | U.S. Pat. No. 5,344,812 |

The active ingredients (a.i.'s) used are known and some of them are commercially available; thidiazuron, for example, from Aventis Crop Science GmbH, Germany, diuron from Griffin, USA, carfentrazone-ethyl from FMC, USA, fluthiacet-methyl from Ihara/Kumiai, Japan and Novartis, Switzerland, and pyraflufen-ethyl from Nihon Nohyako, Japan.

The active ingredients, with specifications about their preparation, mixing and handling, are described, for example, in "The Pesticide Manual" (see above).

Mixtures of thidiazuron and diuron are commercially available (Aventis Crop Science GmbH, Germany). Such mixtures are described, for example, in U.S. Pat. No. 4,613, 354.

Very particular preferred components (B) are fluthiacet-methyl, pyraflufen-ethyl and carfentrazone-ethyl.

The combination of the active ingredients can be used in a manner which is customary per se, for example by spray application of a spray liquor prepared from individual formulations of the active ingredients in a tank mix or of a spray liquor prepared from a mixed formulation of the active ingredients by dilution with water. Methods which are suitable for the application are in particular those which are customary for the application of the individual active ingredients and which allow a joint application.

In principle, the application can also be carried out by successive applications of the individual active ingredients, where the possible interval can be determined in simple preliminary trials. However, preference is given to joint application. If appropriate, the active ingredients can also be used in combination with other active crop-protection agents.

While having the same effect, the application rate of an individual active ingredient in the combination is considerably reduced compared with the application rate of the individual active ingredient in question when used on its own. The optimum choice of the ratio by weight and the application rates depends, for example, on the development stage, on environmental factors and climatic conditions or else on the type of the active crop-protection agents which are additionally employed, if appropriate, and can be determined quickly by the person skilled in the art in simple routine trials.

The application rate for the component (A) is generally in the range from 1 to 500 g of active ingredient (=a.i.)/ha.

For thidiazuron, it is preferably in the range from 10 to 500 g of a.i./ha, particularly preferably from 10 to 300 g of a.i./ha, very particularly preferably from 20 to 200 g of a.i./ha, in particular from 20 to 150 9 of a.i./ha.

In the case of thidiazuron/diuron mixtures (typically in a ratio by weight of 2:1), the application rate is preferably from 10 to 500 g of a.i./ha, particularly preferably from 15 to 300 g of a.i./ha, very particularly preferably from 15 to 220 g of a.i./ha, in particular from 30 to 150 g of a.i./ha.

The application rates for the components (B) can vary within wide limits, depending on the active ingredient, and they are generally between 0.1 and 1000 g of a.i./ha, i.e. they are preferably from 1/2 to 1/40 of the herbicidal application rate recommended in each case.

Preferred application rates for the component (B) are, for example:

a) fluthiacet-methyl:
   0.1–3.0 g of a.i./ha, particularly preferably 0.2–1.0 g of a.i./ha (i.e. less than a third of the amount described for the use as defoliant);

b) pyraflufen-ethyl:
   0.2–5 g of a.i./ha, particularly preferably 0.5–1 g of a.i./ha;

c) carfentrazone-ethyl:
   5–50 g of a.i./ha, particularly preferably 10–30 g of a.i./ha.

The ratios by weight of the components (A): (B) can vary within wide limits, they are usually between 1:0.001 and 1:2, preferably between 1:0.001 and 1:1.5, particularly preferably between 1:0.003 and 1:1, very particularly preferably between 1:0.005 and 1:0.5.

The approximate ratio (A):(B) is preferably for example for fluthiacet-methyl: 1:0.005–1:0.05, in particular 1:0.01–1:0.02 or for (B) 1/30 of the herbicidal application rate, pyraflufen-ethyl: 1:0.01–1:0.1, in particular 1:0.02–1:0.04 or for (B) 1/10 of the herbicidal application rate, carfentrazone-ethyl: 1:0.1–1:1, in particular 1: 0.15–1:0.5 or for (B) 1/3 of the herbicidal application rate.

In addition to the combinations of the components (A) and (B), the compositions acting as defoliants generally comprise other, preferably customary, formulation auxiliaries.

The combinations according to the invention and their individual active ingredients can be formulated in various ways, depending on the prevailing biological and/or chemico-physical parameters. Examples of possible suitable formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), granules (GR) in the form of microgranules, spray granules, coated granules and adsorption granules, water-dispersible granules (WG), water-soluble granules (SG), ULV (ultra-low-volume) formulations, microcapsules and WSBs (water-soluble bags).

These individual types of formulation are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other crop protection agents, such as, for example, insecticides, acaricides, herbicides, fungicides, safeners, other growth regulators and/or fertilizers, for example in the form of a ready mix or a tank mix.

Wettable powders are preparations which are uniformly dispersible in water and which, besides the active ingredient, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane6,6'-disulfonate, sodium dibutyinaphthalenesulfonate or else sodium oleoylmethyltaurinate, in addition to a diluent or inert substance. To prepare the wettable powders, the active ingredients are ground finely, for example in customary equipment such as hammer mills, blower mills and air-jet mills, and simultaneously or subsequently mixed with the formulation auxiliaries.

Emulsifiable concentrates are prepared by dissolving the active ingredients in an organic solvent, for example butanol, cyclohexanone, dimethylformamide, xylene, or else higher-boiling aromatics or hydrocarbons, or mixtures of the organic solvents with the addition of one or more ionic and/or nonionic surfactants (emulsifiers). Examples of emulsifiers which can be used are: calcium salts of alkylarylsulfonic acid such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained for example by grinding the active ingredients with finely divided solid substances, for example talc, natural clays such as kaolin, bentonite and pyrophyllite, or diatomaceous earth. Suspension concentrates can be water- or oil-based. They can be prepared, for example, by wet grinding using commercially available bead mills with or without addition of surfactants as have already been mentioned above, for example in the case of the other types of formulation.

Emulsions, for example oil-in-water emulsions (EW), can be prepared, for example, by means of stirrers, colloid mills and/or static mixers using aqueous organic solvents and, if appropriate, surfactants as have already been mentioned above, for example in the case of the other types of formulation.

Granules can be prepared either by spraying the active ingredients onto adsorptive granulated inert material or by applying active ingredient concentrates to the surface of carriers such as sand, kaolinites or of granulated inert material by means of binders, for example polyvinyl alcohol, sodium polyacrylate or else mineral oils. The active ingredients can also be granulated in the manner which is conventional for the production of fertilizer granules.

Water-dispersible granules are generally prepared by the customary methods such as spray-drying, fluidized-bed granulation, disk granulation, mixing with high-speed mixers and extrusion without solid inert material.

In general, the preparations according to the invention comprise 0.1 to 99% by weight, in particular 0.1 to 95% by weight, of active ingredients of the components (A) and (B).

The active ingredient concentration in wettable powders is, for example, approximately 10 to 90% by weight, the remainder to 100% by weight being composed of customary formulation components. In the case of emulsifiable concentrates, the active ingredient concentration may amount to approximately 1 to 90% by weight. Formulations in the form of dusts comprise, for example, 1 to 80% by weight of active ingredient, in most cases 5 to 60% by weight of active ingredients. Sprayable solutions comprise, for example, 0.05 to 80, in most cases 2 to 50, % by weight of active ingredients. The active ingredient content of water-dispersible granules depends partly on whether the active compounds are in liquid or solid form and on which granulation auxiliaries, fillers and the like are being used. The active ingredient content of the water-dispersible granules amounts to, for example, between 1 and 95% by weight, in most cases between 10 and 80% by weight.

In addition, the abovementioned formulations of active ingredients comprise, if appropriate, adhesives, wetting agents, dispersants, emulsifiers, penetrants, preservatives, antifreeze agents, solvents, fillers, carriers, colorants, antifoams, evaporation inhibitors and pH and viscosity regulators, which are customary in each case.

Components which can also be used in combination with the active ingredients according to the invention in mixed formulations or in a tank mix are, for example, known active ingredients as are described, for example, in Weed Research 26, 441–445 (1986), or "The Pesticide Manual", 11th edition, 1997, and the literature cited therein.

For use, the formulations, which are in commercially available form, are, if appropriate, diluted in the customary manner, for example using water in the case of wettable powders, emulsifiable concentrates, dispersions and water-dispersible granules, and then applied to the plants. This includes specific application variants customary in particular in cotton cultivation, for example the application by plane. Preparations in the form of dusts, granules for soil application or for broadcasting and also sprayable solutions are conventionally not diluted any further with other inert substances prior to use.

The mixtures or compositions according to the invention are preferably employed in suitable crops of useful plants, such as cotton, sunflowers or potatoes. Particular preference is given to the use in crops of cotton.

The method according to the invention for effecting leaf abscission in plants is preferably applied on useful plants, such as cotton, sunflowers or potatoes, particularly preferably on cotton plants.

The mixtures or compositions and the method can, of course, also be employed for treating genetically modified (transgenic) plants, preferably useful plants, particularly preferably cotton, where such plants contain, for example, one or more foreign genes in order to obtain resistance against insecticides and/or herbicides.

The content of the German Patent Application 199 51 428.3 and 199 11 165.0 and the enclosed Abstract are hereby incorporated reference.

The invention is illustrated in more detail by the examples, without being limited thereby.

EXAMPLES

1. Assessment of the Effect and Evaluation of the Synergism

The effect on the plants is evaluated by leaf abscission according to a scale from 0 to 100%:
0%=no noticeable effect when compared with the untreated plant; 100%=all leaves have been dropped.

When assessing the synergism between the active ingredients employed here, the highly different application rates of the individual active ingredients have to be taken into consideration. Thus, it is not expedient to compare the activities of the active ingredient combinations with those of the individual active ingredients in each case at identical application rates. The amounts of active ingredients that can be saved according to the invention become evident from the superadditive increase in activity when using the combined application rates or by the reduction of the application rates of the two individual active ingredients in the combination in comparison to the application rates of the active ingredients applied on their own, the activity remaining the same in each case.

In all instances, a distinction is made in the combinations between the calculated degree of action and the degree of action found. In most cases, the synergistic increase in activity is so high that the activity of the combination considerably surpasses the formal (calculated) total of the activities of the individual ingredients. Such a greatly increased activity was in no way to be expected based on the known activities of the individual active ingredients.

The expected theoretical degree of action of a combination can be approximately estimated by the formula of S. R. Colby (cf. "Calculation of synergistic and antagonistic responses of herbicide combinations", Weeds 15 (1967), pages 20–22).

For combinations of two compounds, this formula is:

$$E = X + Y - \frac{X \cdot Y}{100}$$

where

X=% activity by A at an application rate of x kg/ha;

Y=% activity by B at an application rate of y kg/ha;

E=expected activity by A+B at x+y kg/ha

If the observed activity exceeds the calculated expected activity, the activity of the combination is more than additive, i.e. there is a synergistic effect.

2. Action as Defoliant 2.1. General Procedure

Cotton seeds were sown at a depth of 1 cm and grown in a climatized chamber (14 h of light, temperature during the day: 25° C., at night: 18° C.) until they had reached the 8–10 leaf stage. The active compound combinations were applied using an overhead laboratory sprayer with a Combijet nozzle, in an amount of 300 I/ha.

2.2 Table 1 Mixtures with Fluthiacet-methyl

| No. | Active ingredient (combination) | Dose g/ha | Effect in % 4 days | 5 days |
|---|---|---|---|---|
| 1. | Thidiazuron* (TDZ) | 25 | 5 | 24 |
| 2. | Fluthiacet-methyl (Flu.) | 0.25 | 0 | 0 |
| 3. | Fluthiacet methyl | 0.,5 | 5 | 14 |
| 4. | TDZ + Flu. | 25 + 0.25 | 48 | 81 |
| 5. | TDZ + Flu. | 25 + 0.5 | 57 | 81 |

* ®Dropp 50 WP

2.3. Table 2 Mixtures with Pyraflufen-ethyl

| No. | Active ingredient (combination) | Dose g/ha | Effect in % 3 days | Effect in % 5 days |
|---|---|---|---|---|
| 1. | Thidiazuron* (TDZ) | 25 | 4 | 17 |
| 2. | Pyraflufen-ethyl (Pyra.) | 1 | 0 | 0 |
| 3. | Pyrafluofen-ethyl | 2 | 0 | 0 |
| 4. | TDZ + Pyra. | 25 + 1 | 13 | 17 |
| 5. | TDZ + Pyra. | 25 + 2 | 25 | 25 |

* ®Dropp 50 WP

2.4. Table 3.1 Mixtures with Carfentrazone-ethyl

| No. | Active ingredient (combination) | Dose g/ha | Effect in % 10 days | Effect in % 20 days |
|---|---|---|---|---|
| 1. | Thidiazuron* (TDZ) | 80 | 0 | 8 |
| 2. | Carfentrazone-ethyl (Carf.) | 25 | 0 | 5 |
| 3. | TDZ + Carf. | 80 + 25 | 0 | 30 |

* ®Dropp 50 WP

Table 3.2 Mixtures with Carfentrazone-ethyl

| No. | Active ingredient (combination) | Dose g/ha | Effect in % 6 days | Effect in % 9 days |
|---|---|---|---|---|
| 1. | Thidiazuron* (TDZ) | 25 | 29 | 52 |
| 2. | Carfentrazone-ethyl (Carf.) | 1.5 | 29 | 29 |
| 3. | TDZ + Carf. | 25 + 1.5 | 71 | 81 |

* ®Dropp 50 WP

These experiments clearly demonstrate a synergistic effect.

What is claimed is:

1. A method for effecting leaf abscission in plants which comprises treating plants with a mixture comprising (A) thidiazuron or thidiazuron and diuron and
(B) one or more PPO inhibitors of the formula (I)

W—V    (I), for effecting leaf abscission of plants, where the symbols in the formula (I) have the meanings:

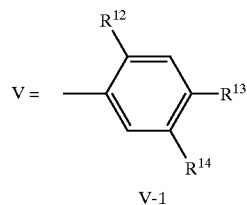

V-1 and

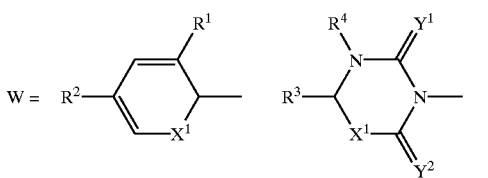

W-1

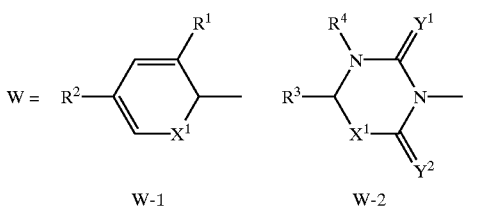

W-2

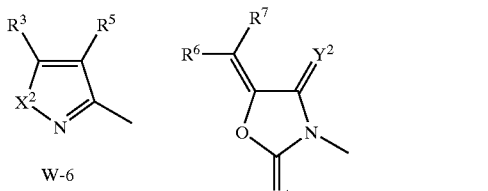

W-6

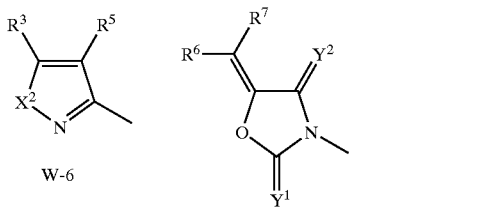

W-7

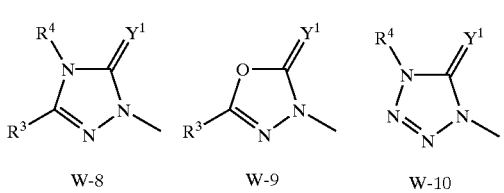

W-8

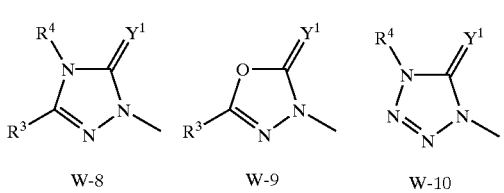

W-9

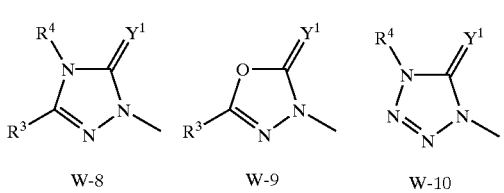

W-10

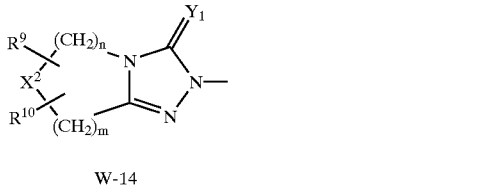

W-14 or

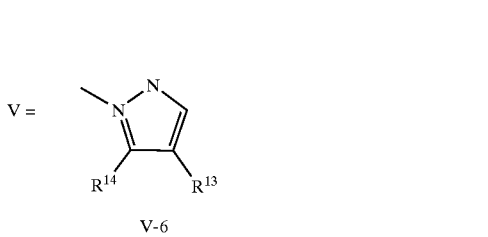

V-6 and

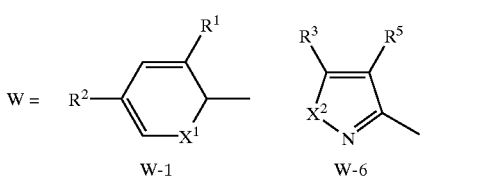

W-1

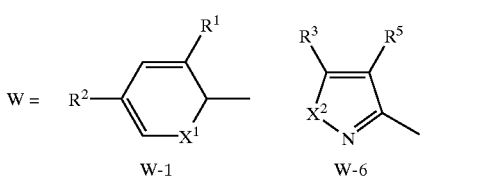

W-6

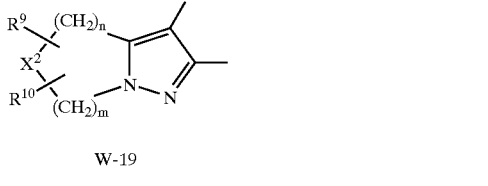

W-19 or

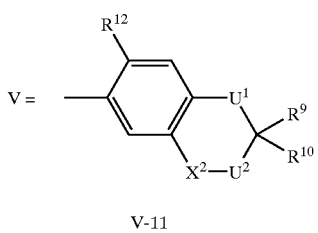

V-11 and

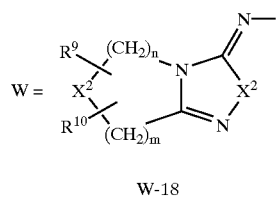

W-18

$R^1$ is hydrogen or halogen;

$R^2$ is halogen, alkyl, alkoxy, haloalkoxy or haloalkyl;

$R^3$ is hydrogen, alkyl, haloalkyl, alkoxy, haloalkoxy, alkyl-S(O)$_n$—, dialkylamino, alkylamino, amino or halogen;

$R^4$ is hydrogen, alkyl, haloalkyl, alkenyl, haloalkenyl, alkynyl, haloalkynyl, formyl, alkyl-CO— or amino;

$R^5$ is hydrogen, halogen, alkyl, haloalkyl or nitro;

$R^6$ is hydrogen, alkyl or haloalkyl;

$R^7$ is hydrogen, alkyl or haloalkyl;

$R^8$ is hydrogen, alkyl, haloalkyl, alkenyl, haloalkenyl, alkynyl or haloalkynyl;

$R^9$ is hydrogen, alkyl, halogen, alkoxy, haloalkyl, haloalkoxy, alkoxycarbonyl, haloalkoxycarbonyl or amino;

$R^{10}$ is hydrogen, alkyl, halogen, alkoxy, haloalkyl, haloalkoxy, alkoxycarbonyl, haloalkoxycarbonyl or amino;

$R^{11}$ is hydrogen or alkyl;

$R^{12}$ is hydrogen, alkyl or halogen;

$R^{13}$ is hydrogen, halogen, alkyl, haloalkyl, alkoxy, haloalkoxy, cyano, nitro, amino, alkylamino, dialkylamino, alkoxycarbonyl, —(C=O)NH$_2$, —(C=S)NH$_2$, hydroxyl, acyloxy, substituted phenyl, substituted phenoxy, substituted benzyl or substituted benzyloxy;

$R^{14}$ is hydrogen, alkyl, haloalkyl, alkoxyalkyl, haloalkoxyalkyl, alkenyl, haloalkoxyalkenyl, alkynyl, haloalkynyl, alkoxy, haloalkoxy, haloalkenyloxy, alkynyloxy, haloalkynyloxy, halogen, —O—COR$^{15}$, —OH, —S(O)$_n$R$^{15}$, —COR$^{17}$, —CONR$^{18}$R$^{19}$, —CO$_2$R$^{20}$, —(CR$^6$R$^7$)$_n$—CO$_2$R$^{20}$, —CR$^{21}$=CR$^{22}$CO$^2$R$^{20}$, —CN, —CR$^{11}$(X$^1$R$^{23}$)(X$^2$R$^{24}$), —NR$^{11}$—(CR$^6$R$^7$)$_n$—CO$_2$R$^{20}$, —O—(CR$^6$R$^7$)$_n$—CO$_2$R$^{20}$, —S(O)$_n$—CR$^{21}$=CR$^{22}$—C(O)NR$^{16}$R$^{17}$, —(CR$^6$R$^7$)$_n$CONR$^{16}$R$^{17}$, —(CR$^6$R$^7$)$_n$—CO$_2$R$^{20}$, —NO$_2$, —NR$^{16}$R$_{17}$, —NR$^{24}$SO$_2$R$^{15}$ or —NR$^{23}$COR$^{15}$;

$R^{15}$ is hydrogen, M, alkyl, haloalkyl, alkenyl, haloalkenyl, alkynyl, haloalkynyl or halogen;

$R^{16}$ is hydrogen, alkyl, aloalkyl, alkenyl, haloalkenyl, alkynyl, haloalkynyl or halogen;

$R^{17}$ is hydrogen, OH, OM, alkyl, haloalkyl, alkenyl, haloalkenyl, alkynyl, haloalkynyl, alkoxyalkyl or haloalkoxyalkyl;

$R^{18}$ is hydrogen, alkyl, alkoxy, alkenyl, haloalkenyl, alkynyl or haloalkynyl;

$R^{19}$ is hydrogen, alkyl, alkoxy or $R^{18}$ and $R^{19}$ together with the nitrogen atom form a 5-, 6- or 7-membered ring which may be interrupted by oxygen or sulfur;

$R^{20}$ is hydrogen, M, alkyl, haloalkyl, alkenyl, haloalkenyl, alkynyl, haloalkynyl, alkoxyalkyl, haloalkoxyalkyl or —(CR$^6$R$^7$)$_n$—CO$_2$R$_{15}$;

$R_{21}$ is hydrogen, alkyl, halogen or CN, $R^{22}$ is hydrogen, alkyl, halogen or CN;

$R^{23}$ is hydrogen or alkyl;

$R^{24}$ is hydrogen, alkyl or $R^{23}$ and $R^{24}$ together are a substituted or else unsubstituted 5-, 6 or 7-membered cyclic acetal or thioacetal;

$R^{25}$ is hydrogen, alkyl, alkoxy, alkenyl, haloalkenyl, alkynyl, haloalkynyl, carbamoyl or thiocarbamoyl;

M is an alkali metal, alkaline earth metal or ammonium ion;

$X^1$ is identical or different and is C-R$^5$ or N;

$X^2$ is identical or different and is CR$^2$R$^6$, O, —S(O)$_n$— or NR$^{25}$;

$Y^1$ is O or S;

$Y^2$ is O or S;

n, are 0, 1 or 2;

$U^1$ is O, S(O)$_n$, NR$^{23}$ or CR$^9$R$^{10}$.

$U^2$ is S(O)$_n$, CR$^9$R$^{10}$ or C=O;

T is CR$^2$R$^6$, NH or NR$^{2.}$

2. The method as claimed in claim 1, wherein the component (A) is thidiazuron.

3. The method as claimed in claim 1, wherein the component (B) is from the following group:

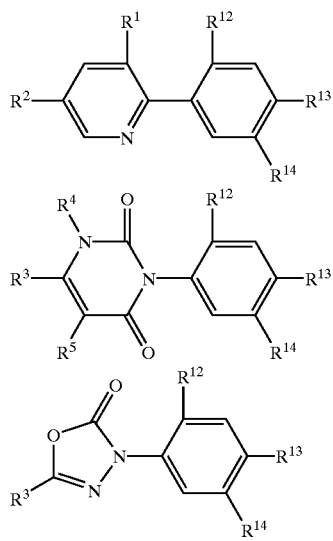

-continued

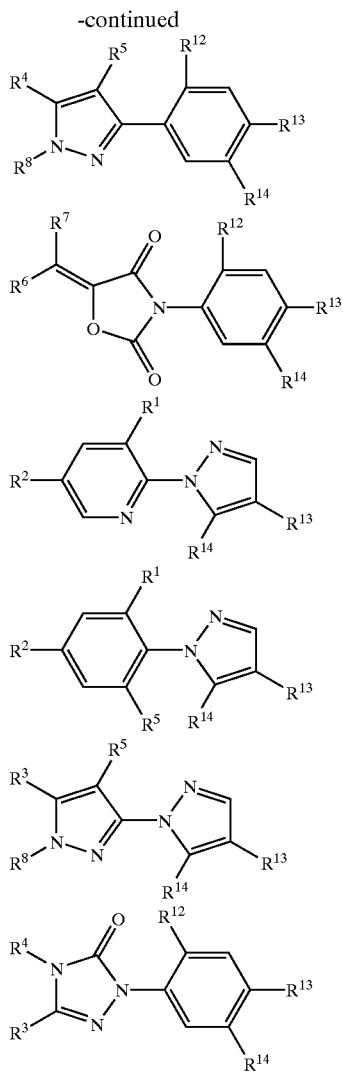

and the symbols and indices have the same meanings as in formula (I) in claim 1.

4. The method for effecting leaf abscission in plants which comprises treating the plants with a mixture comprising
    (A) thidiazuron or thidiazuron and diuron and
    (B) one or more PPO inhibitors selected from the group consisting of pyrazogyl, F-5231, nipyraclofen, KPP-300, sulfentrazone, pentoxazone, flupropacil, M&B-39279, thidiazimin, carfentratzone-ethyl, pyraflufen-ethyl, oxadiargyl, azafenidine, fluazolate, butafenacil, oxadiazon and benzfendizone.

5. A mixture comprising
    (A) thidiazuron or thidiazuron and diuron and
    (B) one or more PPO inhibitors selected from the group consisting of pyrazogyl, F-5231, nipyraclofen, KPP-300, sulfentrazone, pentoxazone, flupropacil, M&B-39279, thidiazimin, carfentratzone-ethyl, pyraflufen-ethyl, oxadiargyl, azafenidine, fluazolate, butafenacil, oxadiazon and benzfendizone.

6. The method as claimed in claim 1, wherein the ration of the components (A):(B) is 1:0.01–1:2.

7. The method as claimed in claim 1, wherein the plant is a cotton plant.

8. The method as claimed in claim 7, wherein the cotton plant is genetically modified.

9. A defoliant, comprising a mixture as defined in claim 1 and formulation auxiliaries.

10. A method for effecting leaf abscission of plants, which comprises treating the plants with a composition as claimed in claim 9.

11. A mixture comprising
    (A) thidiazuron or thidiazuron and diuron and
    (B) one or more PPO inhibitors of the formula (I)

$$W\text{—}V \quad (I),$$

where the symbols in the formula (I) have the meanings:

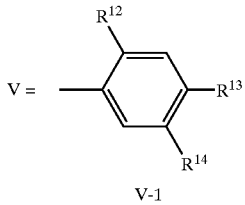

V-1 and

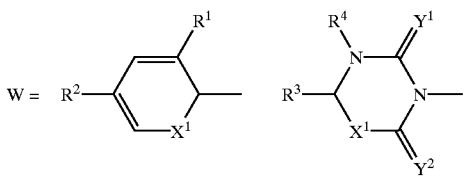

W-1      W-2

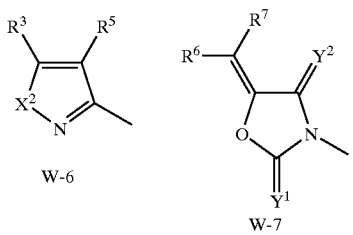

W-6      W-7

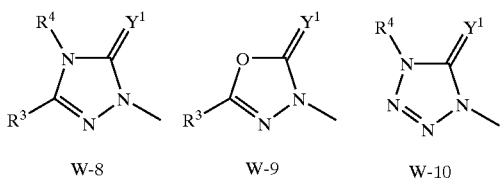

W-8      W-9      W-10

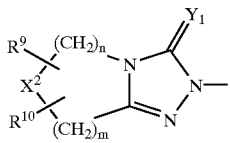

W-14 or

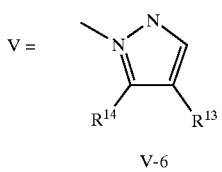

V-6 and

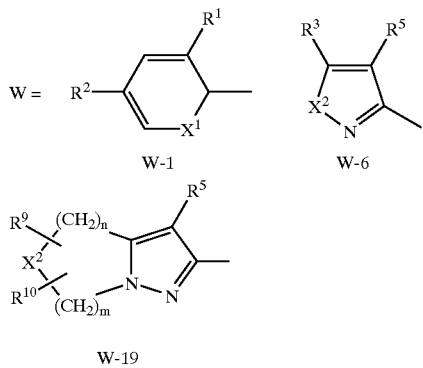

or

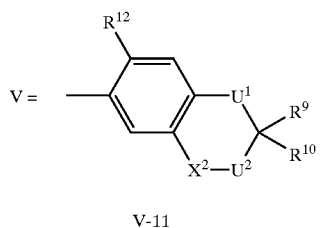

and

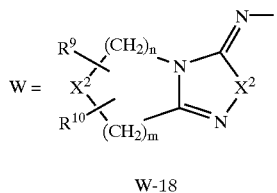

$R^1$ is hydrogen or halogen;
$R^2$ is halogen, alkyl, alkoxy, haloalkoxy or haloalkyl;
$R^3$ is hydrogen, alkyl, haloalkyl, alkoxy, haloalkoxy, alkyl-S(O)$_n$—, dialkylamino, alkylamino, amino or halogen;
$R^4$ is hydrogen, alkyl, haloalkyl, alkenyl, haloalkenyl, alkynyl, haloalkynyl, formyl, alkyl—CO—or amino;
$R^5$ is hydrogen, halogen, alkyl, haloalkyl or nitro;
$R^6$ is hydrogen, alkyl or haloalkyl;
$R^7$ is hydrogen, alkyl or haloalkyl;
$R^8$ is hydrogen, alkyl, haloalkyl, alkenyl, haloalkenyl, alkynyl or haloalkynyl;
$R^9$ is hydrogen, alkyl, halogen, alkoxy, haloalkyl, haloalkoxy, alkoxycarbonyl, haloalkoxycarbonyl or amino;
$R^{10}$ is hydrogen, alkyl, halogen, alkoxy, haloalkyl, haloalkoxy, alkoxycarbonyl, haloalkoxycarbonyl or amino;
$R^{11}$ is hydrogen or alkyl;
$R^{12}$ is hydrogen, alkyl or halogen;
$R^{13}$ is hydrogen, halogen, alkyl, haloalkyl, alkoxy, haloalkoxy, cyano, nitro, amino, alkylamino, dialkylamino, alkoxycarbonyl, —(C=O)NH$_2$, —(C=S)NH$_2$, hydroxyl, acyloxy, substituted phenyl, substituted phenoxy, substituted benzyl or substituted benzyloxy;

$R^{14}$ is hydrogen, alkyl, haloalkyl, alkoxyalkyl, haloalkoxyalkyl, alkenyl, haloalkoxyalkenyl, alkynyl, haloalkynyl, alkoxy, haloalkoxy, haloalkenyloxy, alkynyloxy, haloalkynyloxy, halogen, —O—COR$^{15}$, —OH, —S(O)$_n$R$^{15}$, —COR$^{17}$, —CONR$^{18}$R$^{19}$, —CO$_2$R$^{20}$, —(CR$^6$R$^7$)$_n$—CO$_2$R$^{20}$, —CR$^6$R$^7$)—CR$^{21}$=CR$^{22}$CO$_2$R$^{20}$, —CN, —CR$^{11}$(X$^1$R$^{23}$)(X$^2$R$^{24}$), —NR$^{11}$—(CR$^6$R$^7$)$_n$—CO$_2$R$_{20}$, —O—(CR$^6$R$^7$)$_n$—CO$^2$R$^{20}$, —S(O)$_n$—CR$_{21}$=CR$^{22}$—C(O)NR$^{16}$R$^{17}$, —(CR$^6$R$^7$)$_n$CONR$^{16}$R$^{17}$, —(CR$^6$R$^7$)$_n$CO$_2$R$^{20}$, —NO$_2$, —NR$^{16}$R$^{17}$, —NR$^{24}$SO$_2$R$^{15}$ or —NR$^{23}$COR$^{15}$;
$R^{15}$ is hydrogen, M, alkyl, haloalkyl, alkenyl, haloalkenyl, alkynyl, haloalkynyl or halogen;
$R^{16}$ is hydrogen, alkyl, haloalkyl, alkenyl, haloalkenyl, alkynyl, haloalkynyl or halogen;
$R^{17}$ is hydrogen, OH, OM, alkyl, haloalkyl, alkenyl, haloalkenyl, alkynyl, haloalkynyl, alkoxyalkyl or haloalkoxyalkyl;
$R^{18}$ is hydrogen, alkyl, alkoxy, alkenyl, haloalkenyl, alknyl or haloalkynyl;
$R^{19}$ is hydrogen, alkyl, alkoxy or
$R^{18}$ and $R^{19}$ together with the nitrogen atom form a 5-, 6- or 7-membered ring which may be interrupted by oxygen or sulfur;
$R^{20}$ is hydrogen, M, alkyl, haloalkyl, alkenyl, haloalkenyl, alkynyl, haloalkynyl, alkoxyalkyl, haloalkoxyalkyl or —(CR$^6$R$^7$)$_n$—CO$_2$R$^{15}$;
$R^{21}$ is hydrogen, alkyl, halogen or CN;
$R^{22}$ is hydrogen, alkyl, halogen or CN;
$R^{23}$ is hydrogen or alkyl;
$R^{24}$ is hydrogen, alkyl or
$R^{23}$ and $R^{24}$ together are a substituted or else unsubstituted 5-, 6- or 7-membered cyclic acetal or thioacetal;
$R^{25}$ is hydrogen, alkyl, alkoxy, alkenyl, haloalkenyl, alkynyl, haloalkynyl, carbamoyl or thiocarbamoyl;
M is an alkali metal, alkaline earth metal or ammonium ion;
$X^1$ is identical or different and is C-R$^5$ or N;
$X^2$ is identical or different and is CR$^2$R$^6$, O, —S(O)$_n$—or NR$^{25}$;
$Y^1$ is O or S;
$Y^2$ is O or S;
n, are 0, 1 or 2;
$U^1$ is O, S(O)$_n$, NR$^{23}$ or CR$^9$R$^{10}$.
$U^2$ is S(O)$_n$, CR$^9$R$^{10}$ or C=O;
T is CR$^2$R$^6$, NH or NR$^2$.

12. A mixture as claimed in claim 11, wherein the components (A) and (B) are present in synergistically effective amounts.

13. A method for effecting leaf abscission in plants which comprises treating the plants with a mixture comprising synergistically effective amounts of thidiazuron and pyraflufen-ethyl.

14. A method for effecting leaf abscission in plants which comprises treating the plants with a mixture comprising synergistically effective amounts of thidiazuron and carfentrazone-ethyl.

15. A mixture comprising synergistically effective amounts of thidiazuron and pyraflufen-ethyl.

16. A mixture comprising synergistically effective amounts of thidiazuron and carfentrazone-ethyl.

* * * * *

UNITED STATES PATENT AND TRADEMARK OFFICE
CERTIFICATE OF CORRECTION

PATENT NO.   : 6,444,613 B1
DATED        : September 3, 2002
INVENTOR(S)  : Feurer et al.

It is certified that error appears in the above-identified patent and that said Letters Patent is hereby corrected as shown below:

Column 13,
Table 2, the chemical structure named "pyrazogyl (proposed) or …"
The structure:

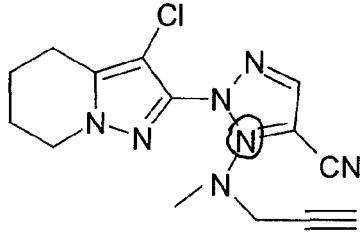

should be replaced by:

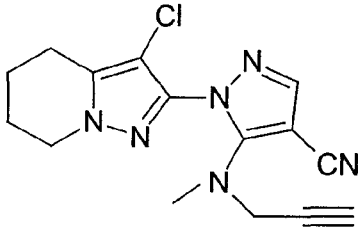

Column 25,
Line 58, "–$CR^{21}=CR^{22}CO^{2}R^{20}$" should read -- –$CR^{21}=CR^{22}CO_2R^{20}$ --;
Line 62, "$NR^{16}R_{17}$" should read -- $NR^{16}R^{17}$ --;

Column 26,
Line 36, "n, _  are 0, 1 or 2" should read -- n, m  are 0, 1 or 2 --;

Column 27,
Lines 51 and 59, "carfentratzone-ethyl" should read -- carfentrazone-ethyl --;

UNITED STATES PATENT AND TRADEMARK OFFICE
CERTIFICATE OF CORRECTION

PATENT NO. : 6,444,613 B1
DATED : September 3, 2002
INVENTOR(S) : Feurer et al.

It is certified that error appears in the above-identified patent and that said Letters Patent is hereby corrected as shown below:

<u>Column 30,</u>
Line 5, "$-CO_2R^{20}, -(CR^6R^7)_n-CO_2R^{20}, -CR^6R^7)$," should read -- $CO_2R^{20}, -(CR^6R^7)_n-CO_2R^{20}$ --;
Line 8, "$-NR^{11}-(CR^6R^7)_n-CO_2R_{20}$" should read -- "$-NR^{11}-(CR^6R^7)_n-CO_2R^{20}$ --;
Line 9, "$-(CR^6R^7)_n-CO^2R^{20}, -S(O)_n-CR_{21}=CR^{22}-C(O)$" should read -- $-(CR^6R^7)_n-CO_2R^{20}, -S(O)_n-CR^{21}=CR^{22}-C(O)$ --;
Line 47, "n, _ are 0, 1 or 2" should read -- n, m are 0, 1 or 2 --;

Signed and Sealed this

First Day of July, 2003

JAMES E. ROGAN
*Director of the United States Patent and Trademark Office*